(12) United States Patent
Fell et al.

(10) Patent No.: US 6,558,421 B1
(45) Date of Patent: *May 6, 2003

(54) SURGICALLY IMPLANTABLE KNEE PROSTHESIS

(76) Inventors: Barry M. Fell, 7124 Red Top Rd., Hummelstown, PA (US) 17036; Richard H. Hallock, 1660 Woodhaven Dr., Hummelstown, PA (US) 17036

(*) Notice: Subject to any disclaimer, the term of this patent is extended or adjusted under 35 U.S.C. 154(b) by 0 days.

This patent is subject to a terminal disclaimer.

(21) Appl. No.: 09/664,939

(22) Filed: Sep. 19, 2000

Related U.S. Application Data (63) Continuation of application No. 09/297,943, filed as application No. PCT/US99/07309 on Apr. 2, 1999, now Pat. No. 6,206,927.

(51) Int. Cl.⁷ .................................................. A61F 2/38
(52) U.S. Cl. ................................. 623/14.12; 623/20.14
(58) Field of Search ........................ 623/20.14–20.17, 623/20.21, 20.22, 20.24–20.33, 20.39–20.41

(56) References Cited

U.S. PATENT DOCUMENTS

| | | | | |
|---|---|---|---|---|
| 4,085,466 A | * | 4/1978 | Goodfellow et al. | 623/20 |
| 4,224,696 A | * | 9/1980 | Murray et al. | 623/20 |
| 4,808,185 A | * | 2/1989 | Penenberg et al. | 623/20 |
| 4,865,607 A | * | 9/1989 | Witzel et al. | 623/20 |
| 4,883,488 A | * | 11/1989 | Bloegaum | 623/20 |
| 5,358,530 A | * | 10/1994 | Hodorek | 623/20 |
| 5,387,240 A | * | 2/1995 | Pottenger et al. | 623/20 |
| 5,658,342 A | * | 8/1997 | Draganich et al. | 623/20 |
| 5,871,542 A | * | 2/1999 | Goodfellow et al. | 623/20 |
| 5,871,543 A | * | 2/1999 | Hofmann | 623/20 |
| 5,879,394 A | * | 3/1999 | Ashby et al. | 623/20 |
| 6,090,144 A | * | 7/2000 | Letot et al. | 623/20 |
| 6,165,223 A | * | 12/2000 | Metzger et al. | 623/20.27 |
| 6,206,927 B1 | * | 3/2001 | Fell et al. | 623/20.29 |

* cited by examiner

Primary Examiner—Kevin Shaver
Assistant Examiner—Michael B. Priddy
(74) Attorney, Agent, or Firm—Brooks & Kushman P.C.

(57) ABSTRACT

A self-centering meniscal prosthesis device suitable for minimally invasive, surgical implantation into the cavity between a femoral condyle and the corresponding tibial plateau is composed of a hard, high modulus material shaped such that the contour of the device and the natural articulation of the knee exerts a restoring force on the free-floating device.

20 Claims, 3 Drawing Sheets

SURGICALLY IMPLANTABLE KNEE PROSTHESIS

This is a continuation of application Ser. No. 09/297,943 filed on May 10, 1999 now U.S. Pat. No. 6,206,927 B1 which is a 371 of PCT/US99/07309 filed Apr. 02, 1999.

TECHNICAL FIELD

The present invention pertains to prosthetic devices. More particularly, the invention pertains to self-centering knee joint prostheses which may be surgically implanted between the femoral condyle and tibial plateau of the knee.

BACKGROUND ART

Articular cartilage and meniscal cartilage provide the mobile weight bearing surfaces of the knee joint. Damage to these surfaces is generally due to genetic predisposition, trauma, and/or aging. The result is usually the development of chondromalacia, thinning and softening of the articular cartilage, and degenerative tearing of the meniscal cartilage. Various methods of treatment are available to treat these disease processes. Each option usually has specific indications and is accompanied by a list of benefits and deficiencies that may be compared to other options. Nonsteroidal anti-inflammatory drugs (NSAIDS), cortisone injections, arthroscopic debridement, osteotomy, unicompartmental knee replacement, and total knee replacement have all been used to treat the disease depending on the severity of the process.

Currently, there is a void in options used to treat the relatively young patient with moderate to severe chondromalacia involving mainly one compartment of the knee. Some patients cannot tolerate or do not want the risk of potential side effects of NSAIDS. Repeated cortisone injections actually weaken articular cartilage after a long period of time. Arthroscopic debridement alone frequently does not provide long lasting relief of symptoms. Unicompartmental and bicompartmental total knee replacements resect significant amounts of bone and may require revision surgery when mechanical failure occurs. Revision total knee replacement surgery is usually extensive and results in predictably diminished mechanical life expectancy. Therefore, it is best to delay this type of bone resecting surgery as long as possible.

DESCRIPTION OF THE RELATED ART

Several approaches have generally been employed in the past to correct the aforementioned problems. The first approach involves repair of articular or meniscal cartilage. Repair of the articular cartilage by surgically transplanting autogenous or autologous osteochondral core grafts has had limited success, but is not always indicated. Meniscus repair using barbed "arrows" such as the Bionix "Meniscus Arrow" has been used for "bucket-handle" tears, but is not applicable to other knee joint problems. Thus, these methods have limited scope and are generally confined to unique kinds of damage.

In the second approach, a unicompartmental or bicompartmental bone resection is performed, replacing the bone with a load bearing prosthesis. This resection may be performed only on the femoral condyle, or may include the tibial plateau. In either case, the resection involves considerable surgical skill, and results in prosthetic devices physically anchored into the bone structure. Not only is such reconstruction expensive major surgery, but moreover, the mechanical means of attachment may fail as the patient grows older. Examples of prostheses utilized in such methods are those disclosed in Ries, U.S. Pat. No. 5,549,688; Cloutier, U.S. Pat. No. 4,207,627; and Shah, U.S. Pat. No. 5,263,987.

The third approach has been to replace the meniscal cartilage ("meniscus") with a soft, compliant material. In theory, such devices cushion the femoral and tibial bearings surfaces and distribute loads uniformly over a large portion of the knee joint due to the ability of these devices to elastically deform. This ability to deform can also be a detriment, however, when it is desired to isolate portions of the articular cartilage or bone surfaces from loads. Moreover, such devices are prone to tearing or disintegration under repeated stress due to their low tensile strength and modulus. Being flexible, they may be ejected from the meniscular cavity if not anchored in place. Anchoring devices may create an area susceptible to fatigue fracture, causing dislocation of the prosthesis and further damage to the knee joint.

Thus, for example, Kenny, in U.S. Pat. No. 4,344,193, discloses a meniscus prosthetic device of a rubbery material such as silicone rubber, having two prominences, which interact with a space defined by the geometry of the femoral condyles. This interaction involving the prominences, together with surgical sutures secured to surrounding soft tissue, are said to maintain the meniscus fixed in the proper location. A porous border, into which fibrous tissue ingrowth is theorized to occur, may also assist in performing the locating function. A similar approach is disclosed in Stone, U.S. Pat. Nos. 4,880,429; 5,007,934; and 5,158,574, where the meniscus comprises a porous matrix of biocompatible fibers or fibers of natural origin to act as a "scaffold" for regrowth of native meniscal tissue. The device is manufactured with an outer contour substantially the same as that of a native meniscus.

In Kenny, U.S. Pat. No. 5,171,322, a meniscus prosthetic device is composed of a biocompatible, deformable, flexible and resilient material having the shape of a natural meniscus, but having a tail which may extend through holes bored in the bone to anchor the device. In similar fashion, Wall, in U.S. Pat. No. 4,502,161, discloses an extra-articular extension attached to the bone outside the joint; while Richmond, U.S. Pat. No. 4,919,667 employs natural fibrous growth to positively anchor his device, again shaped like a natural meniscus. Schwartz, U.S. Pat. No. 5,344,459 utilizes a soft device of rings that are inflatable with air, liquid, or semi-solid to provide a gel cushion between joint surfaces.

The previously described devices of the prior art second approach all utilize soft, cushiony materials which are anchored in place by mechanical means or through tissue regrowth to prevent movement of the device or its extrusion (spitting) from the compartments. One device which differs from those previously described, and which has been used in knee reconstruction, is the so-called "MacIntosh knee," where a hard prosthesis is located by means of protruding ridges, generally in the form of a cross, which nest into corresponding grooves cut into the tibial plateau to prevent movement of the device. These devices have been found to cause pain in the knee joint. This type of prosthetic device and the so-called "McKeever" device require very invasive surgical procedures, require large arthrotomy, require bone and tissue resection, and are irreversible processes.

SUMMARY OF THE INVENTION

The present invention pertains to a meniscal device suitable for surgical implantation into a knee compartment defined by the space between a femoral condyle and the respective tibial plateau. The device is a hard, self-centering meniscal device devoid of physical means that fix its location. The device does not have the natural shape of the meniscus, but rather is designed such that articulation of the knee results in a modest amount of lateral/medial and anterior/posterior translation, relative to the tibial plateau, of the device. The present invention also pertains to a process for the manufacture of suitable meniscal devices.

DESCRIPTION OF THE PREFERRED EMBODIMENTS

The prosthetic meniscal devices of the subject invention are unicompartmental devices suitable for minimally invasive, surgical implantation. By the term "meniscal devices" is meant that the devices are positioned within a compartment in which a portion of the natural meniscus is ordinarily located. The natural meniscus may be maintained in position or may be wholly or partially removed, depending upon its condition. Under ordinary circumstances, pieces of the natural meniscus which have been torn away are removed, and damaged areas may be trimmed as necessary. In somewhat rarer instances, the entire portion of the meniscus residing in the meniscal cavity may be removed. Thus the term "meniscal device" is descriptive of the location of the device rather than implying that it is a replacement for, or has the shape of, the natural meniscus. Actually, as described hereinafter, the shape of the meniscal device is not the same as the natural meniscus, and in most cases, will not entirely replace the meniscus.

By the term "unicompartmental" is meant that each device is suitable for implantation into but one compartment defined by the space between a femoral condyle and its associated tibial plateau. In other words, the device is not a "bicompartmental" device which, in one rigid device, could be inserted into both of the two femoral condyle/tibial plateau compartments. In many, if not most cases, a device will be inserted into one compartment only, generally the medial compartment, as the meniscus and associated articular surfaces in these compartments (left knee medial and right knee medial compartments) are most subject to wear and damage. However, it is possible to insert two separate devices into the medial and lateral compartments of the same knee, or to use two such devices that are mechanically but non-rigidly linked.

The meniscal devices are translatable but self-centering. By "translatable" is meant that during natural articulation of the knee joint, the device is allowed to move, or change its position. Thus, the device is devoid of means of physical attachment which limit its movement, for example, screws, mating ridges and depressions, porous areas to accommodate tissue regrowth, and the like.

By the term "self-centering" is meant that upon translation from a first position to a second position during knee articulation, the device will return to substantially its original position as the articulation of the knee joint is reversed and the original knee position is reached. Thus, the device will not progressively "creep" towards one side of the compartment in which it is located. Rather, the angle of attack of the femoral condyle and/or tibial plateau bearing surfaces against the meniscal device will ensure that the device reversibly translates during articulation, maintaining the meniscal device, on average, in the same location for any given degree of knee articulation.

Contrary to most devices which are composed of soft, compliant material designed to assume the function of the natural meniscus which they replace, the present device is composed of relatively hard, relatively high modulus material. Suitable materials are, for example, steel, ceramics, and reinforced and non-reinforced thermoset or thermoplastic polymers. The device need not be made of a single material, but composite structures of steel/thermoplastic, steel/ceramic, ceramic/polymer, etc., may be used. Alternatively, composites of above materials with biologically active surfaces or components may be used. Biologically active components include surfaces that may contain pharmaceutical agents to stimulate cartilage growth or retard cartilage degeneration that may be delivered at once or in a timed-release manner.

Generally, portions of the devices expected to have the most wear due to either greater movement relative to the mating surface, i.e., relative to the femoral condyle or tibial plateau; or high stress, may be made of stronger, more abrasion resistant material than the remainder when composite structures are used. This method may be ideal for use in conjunction with cultured chondrocyte implantation (cartilage cells used as seeds) or osteochondral transplantation or mosaicplasty. Moreover, when the locus of damage to the articular cartilage or to portions of the bone structure are known, the relatively constant radius of the surface of the meniscal device will bridge the defective areas at these loci, thus redistributing load to healthy tissue and allowing inflamed, diseased, or other damaged areas to regenerate.

For example, a portion of the femoral condyle, tibial plateau, articular cartilage, etc., may have been damaged or may experience tissue degeneration. The continued load experienced at such points and the wear experienced as the knee flexes will substantially hinder the regeneration of healthy tissue. If suitable biologically active materials, chondrocytes, etc. are applied to the damages or degenerated surface to assist in tissue regeneration, these will, under ordinary circumstances, be rapidly dissipated. If a flexible, cushiony material is inserted within the knee compartment, the damaged area will still experience intimate contact with the damaged area under static loads, and will also experience continued wear and abrasion under non-static conditions.

Under such circumstances, active substances will be rapidly dissipated. However, more importantly, newly regenerated articular cartilage not having the necessary density or cohesiveness to withstand wear, will be rapidly eroded away.

The subject invention meniscal load distributing devices may be supplied with a contour which allows the devices to act as a surface which distributes the loads evenly over regions of healthy articular cartilage, in general, abutting and bridging surfaces where articular cartilage degeneration or damage has occurred. Active substances may be applied at once or in a timed-release manner to the degenerated or damaged articular cartilage surface by means of, or in conjunction with, the meniscal device. Because the recess or shape of the meniscal device protects the damaged area from loads and wear, tissue regeneration may occur without disturbance. The regenerating tissue will have time to mature and crosslink into a fully developed matrix. Moreover, as regeneration proceeds, the regenerating tissue will assume a shape dictated by the shape of the meniscal load-distributing device. Growth under these circumstances has the greatest potential for dense, ordered growth most closely replicating the original surface.

The hardness of the meniscular devices is preferably higher than Shore 60 D. The shore hardness may range from that common for engineering grade plastics to hardened steel and titanium, and preferably on the portion of the Rockwell hardness scale typical of steels, hard plastics and ceramic materials. From the high hardness desired of the meniscal device, it is readily apparent that the devices function in a manner completely different from those of the prior art such as Stone, Dedo, Schwartz, Richmond, and Kenny. The purpose of the devices of the subject invention is to achieve a span-like effect to bridge the defective areas. However, in a composite variation, any single component (like a bioactive material component) may be softer than the supporting material. Rather than deforming to distribute a load relatively equally on the mating surfaces, the meniscal devices of the present invention function as rigid, substantially non-deforming, self-centering bearings, which do not necessarily spread the load uniformly, but rather may concentrate the load upon desired points, spanning areas of imperfection. If a soft and/or low modulus elastomer or thermoplastic is used for the entire device, not only is the load not concentrated on healthy tissue, but moreover, damaged areas due to wear and/or degeneration will also be subjected to loading, decreasing the opportunity for the body's natural regenerative capability to function.

The high modulus of the subject meniscal devices thus allows for the provision of recessed or non-contacting areas of the device to encourage articular cartilage regeneration. In softer, lower modulus materials, the naturally occurring loads, which may exceed 1000 lbs/in$^2$ in certain cases, will cause the softer devices to deform and allow ordinarily non-contacting areas to contact bone or cartilage for which contact is desired to be avoided. A flexural modulus of elasticity for load bearing portions of the meniscal devices should therefore be preferably greater than $2 \times 10^5$ psi, and more preferably greater than $3 \times 10^6$ psi. Portions of the device not exposed to the highest loads may be made of lower modulus materials, which may be softer as well, e.g., in a non-limiting sense, nylon, polyurethane, polypropylene, polyester, and the like, optionally fiber reinforced.

As indicated previously, the meniscal devices of the subject invention may be manufactured so as to substantially contain or have deposited thereon, a biologically or pharmaceutically active material. This is particularly suitable when the device bridges a defective area of bone or articular cartilage. In such cases, the meniscal device may be provided with a coating containing a biologically or pharmaceutically active material, for example one that promotes tissue regrowth or one that decreases inflammation. Such materials may also, and more preferably, be contained in a portion of the meniscal device. The portion may be filled with medication, or may be filled with a gel, paste, or soft polymer material that releases medication over a period of time. Preferably, this medically active portion does not actually contact, or minimally contacts, the damaged tissue. This freedom from contact is made possible by the surrounding bearing surfaces. Coatings may also be of a gel, paste, or polymer containing time-release medicaments. Biologically and pharmaceutically active materials are identified subsequently herein as "active materials."

Figure 4:
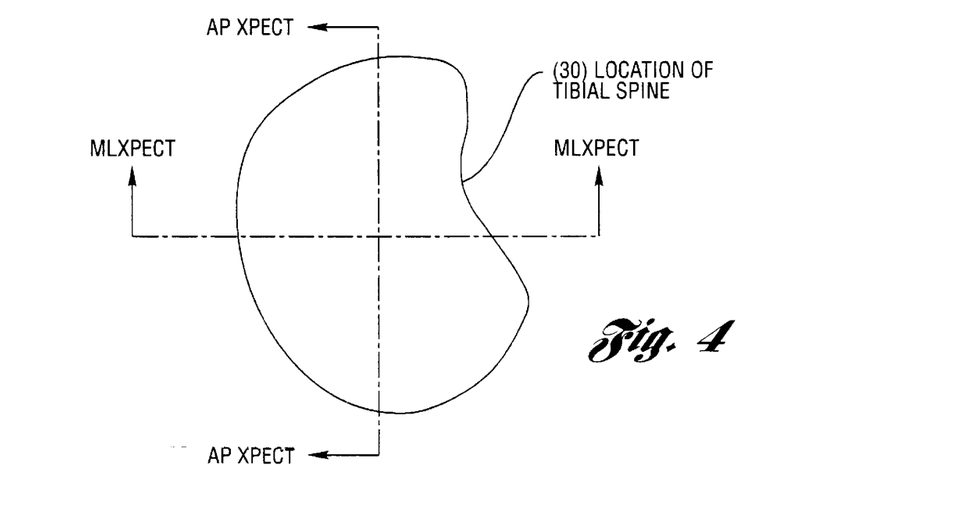
FIG. 4 illustrates the distorted elliptical (kidney bean) shape of a device.
Figure 5:
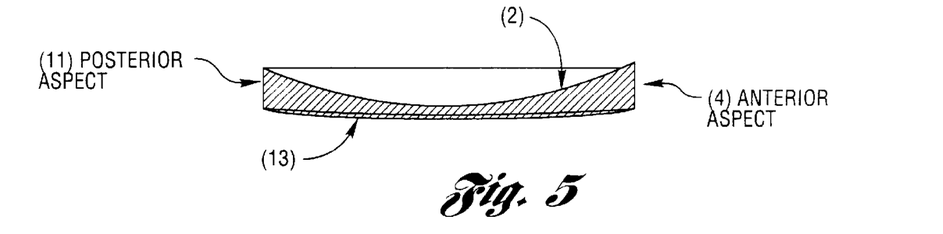
FIG. 5 and 6 illustrate cross-sections of a device in orthogonal planes.
Figure 6:
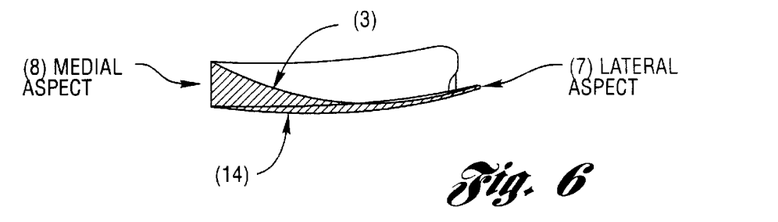
Figure 8:
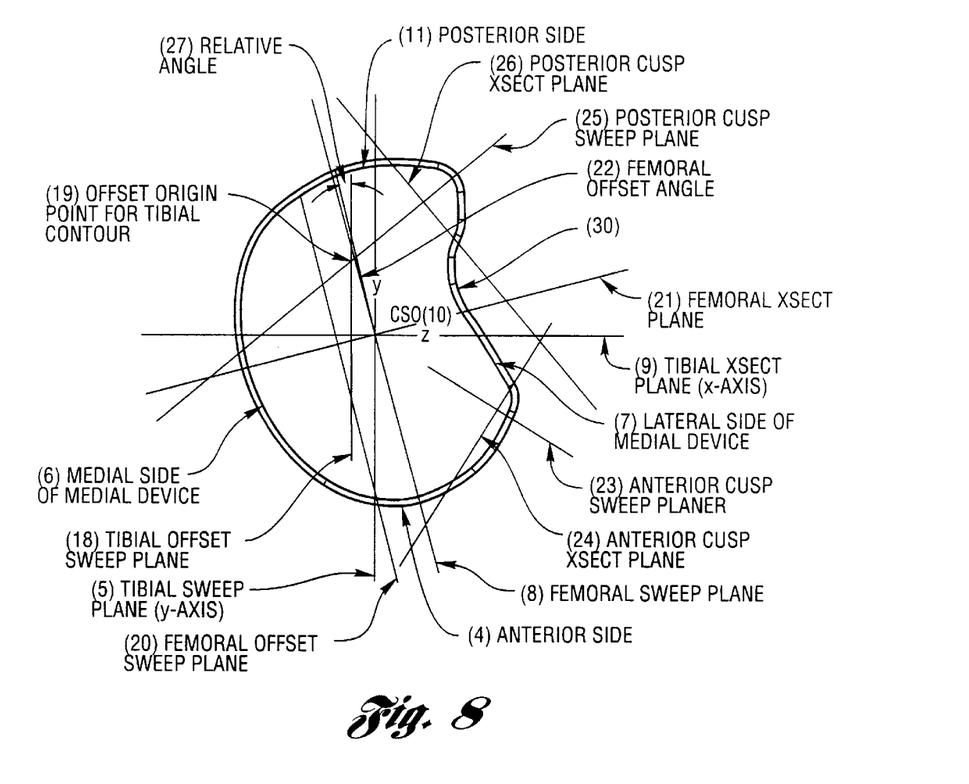
FIG. 8 illustrates the axes and planes which may be used to generate the shape of a meniscal device in one embodiment of the subject invention.
Figure 9:
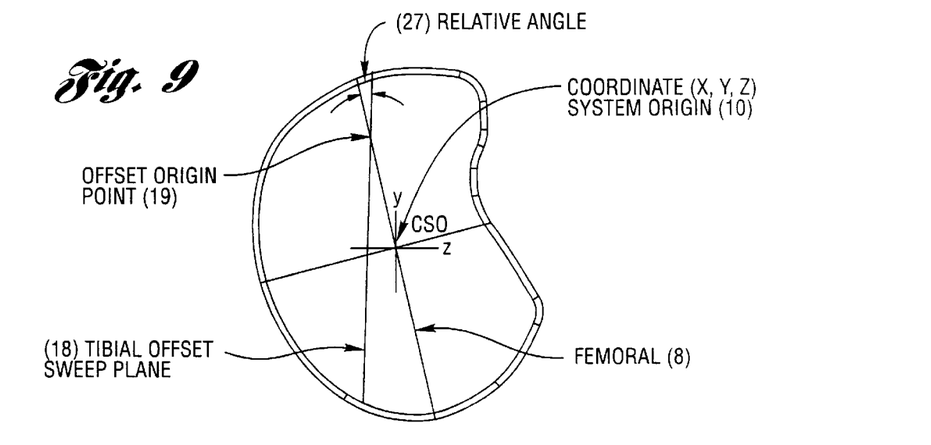
FIG. 9 illustrates the relationship of various coordinates and axes of a device viewed perpendicular to the plane of the device.

The actual shape of the meniscal devices may be tailored to the individual. Individuals with high varus (heels in, knees out—typical degenerative arthritis or valgus (heels out, knees in) deformation due to wear, degeneration, or disease, may require meniscal devices which are of considerably greater thickness over the portions where wear is most advanced. In youthful patients, where trauma-induced damage rather than severe wear or degeneration has occurred, differences in device thickness will be more moderate. In general, the meniscular devices are kidney-shaped when viewed from above, and have a negative meniscus shape when viewed from the side, i.e.; the thickness along the periphery of the device is greater than the thickness along the center of the device. The kidney-shape in plan (FIG. 4) may be described generally as elliptical, the shape resembling a distorted ellipse, with the distortion (30) (FIG. 8) generally determined by the shape and location of the tibial spine. The device covers not only the peripheral areas of the meniscus but also the central weight bearing surface of the femoral condyle and tibial plateau.

Figure 7:
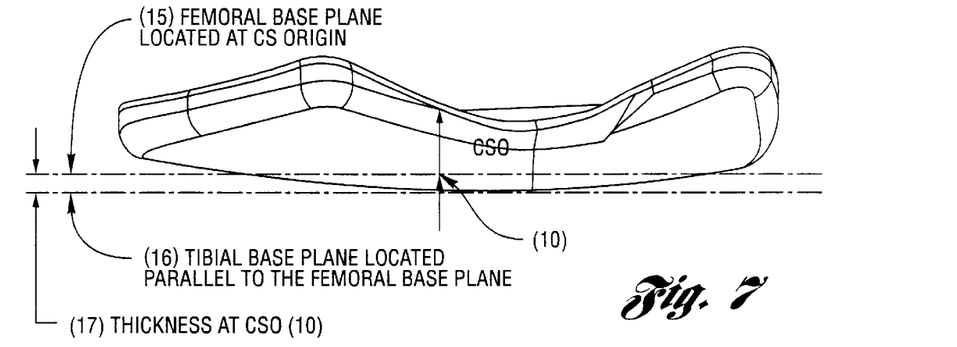
FIG. 7 illustrates a device contour and its relationship with the femoral and tibial base planes.

For example, the inside (central) thickness ((17) FIG. 7) may range from about 0.010 inches (0.25 mm) to 0.20 inches (5 mm) over a somewhat elliptical area measuring, for a hypothetical average knee, about 1.0 inches (25.4 mm) along the minor axis and 1.40 inches (35.6 mm) across the major axis. The meniscal devices are generally thicker at the posterior portion (11) of the device (the portion of the periphery nearest the posterior of the knee joint) as compared to the lateral (7) or medial (6) sides. The medial(6) side of a medial compartment device, (lateral side of a lateral compartment device) is generally thicker than the lateral (7)(the side along the tibial spine) side, and the medial (6) and anterior (4) sides are generally of the same thickness. The outside thickness may range up to 0.40 inches (10 mm) in some cases.

The edges of the device are rounded rather than presenting the sharp corners of the devices of U.S. Pat. No. 5,158,574. This rounded periphery is necessary due to the fact that the device will be allowed to move within the cavity. Movement of a device having a periphery with sharp corners would result in the potential for severe damage to the surrounding tissue and articular surfaces, in addition to causing pain. The "kidney shaped" devices are termed "substantially elliptical" as that term is used herein. The "depression" in the elliptical shape on the part of the device which will be proximate to the tibial spine (30 in FIG. 4) will vary from patient to patient. It is possible, due to the great range of variability of human anatomy that this depression might be absent in devices for some patients. However, the overall shape in plan is substantially elliptical regardless.

Figures 1, 2:
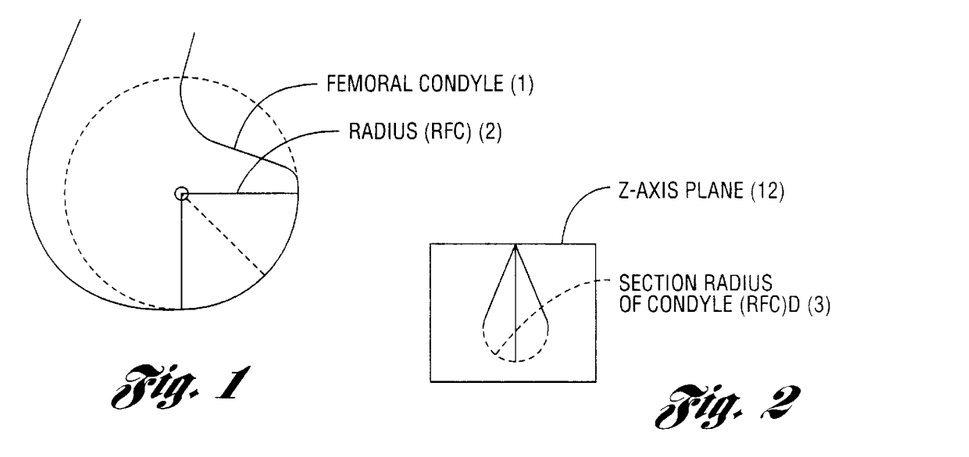
FIG. 1 depicts the relationship between the radius (RFC) and the femoral condyle.
FIG. 2 illustrates the shape of the femoral condyle in cross section.

As shown for the femoral and tibial surfaces of the device in FIG. 1 and in FIG. 2, the surfaces of the meniscal device generally are convex or concave in a symmetrical manner, i.e., their radius of curvatures in a given direction, are in general, relatively constant. There are generally four directions of radii need to describe the two surfaces, as illustrated in FIGS. 1–9, the femoral anterior to posterior ($R_{FC}$)(2), the tibial anterior to posterior ($R_{TC}$)(13), the femoral medial to lateral ($R_{FCX}$)(3) and the tibial medial to lateral($R_{TCX}$)(14). Typical values would be $R_{FC}$ from 1.1–2.0 inches (28–51 mm), $R_{FCX}$ from 0.5–1.5 inches (12.7–38 mm), $R_{TP}$ from 6–12 inches (15.2–30.5 cm) and $R_{TPX}$ from 1.5–3 inches (38–76 mm). An example of a device would have the following values: $R_{FC}$=1.6 inches (40.6 mm), $R_{FCX}$=1.2 inches (30.5 mm), $R_{TP}$=10 inches (25.4 cm) and $R_{TPX}$=2.3 inches (58.4 mm). However, it is also necessary to allow for an increasing or decreasing radius to accommodate a specific patient's needs. For example, the $R_{FC}$ of such a device may have a radius of 1.3 inches (33 mm) at the most anterior point of the device but may increase in a geometric manner to a radius of 1.8 inches (45.7 mm) at its most posterior aspect. Simultaneously, the $R_{FCX}$ may have a radius of 0.8 inches (20.3 mm) at the most anterior point of the device but may increase in a geometric manner to a radius of 1.3 inches (33 mm) at its most posterior aspect. Such transitions of radii would occur in a smooth manner consistent with a bearing surface.

The asymmetric shape of the device still allows for a good fit to the femoral condyle as the femoral condyle has an almost constant radius of curvature, as shown in FIG. 1, in the area that the tibial plateau moves against. This radius of curvature, when viewed from above, as in FIG. 3, generally describes the contour angle (or the predominent orientation of the radius of curvature along the anterior to posterior direction) of the femoral condyle. In addition, the posterior rim and the large radius of the tibial side of the device prevents the device from "spitting". Thus, regardless of whether the knee is in extension or flexion, the degree of "tightness" remains the same and the device will not restrain or limit the motion of the knee. Further, the surface area of the femoral side may be smaller than its corresponding tibial surface along the anterior, medial (medial side of a medial device) and posterior aspects of the device. In such a manner, the femoral side of the device would be closer in size to the femoral condyle, while the tibial plateau would remain fully covered thus, giving the device a "sloped" shape along the aforementioned edges. Such a device shape would be suitable for use with certain anatomical shapes as well as for use with a partially or fully intact meniscus. The term "substantially immune from spitting" means that the device, without any physical attachment to the knee, will ordinarily remain in place in the knee compartment over the normal range of activity expected of the knee.

Figure 3:
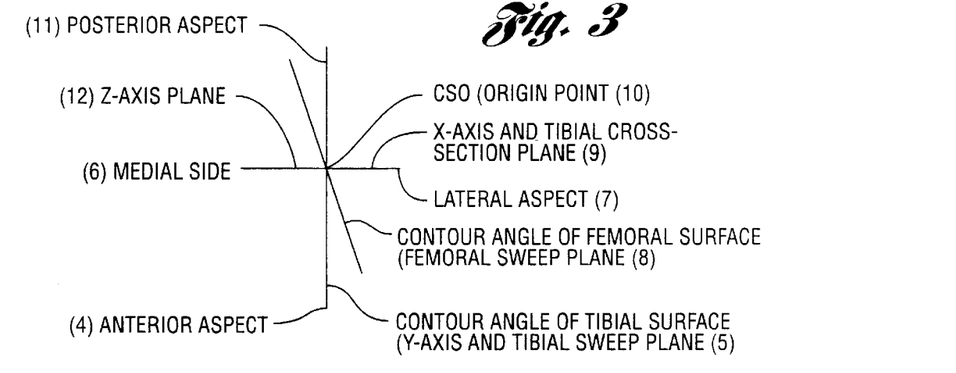
FIG. 3 illustrates certain spatial relationships with respect to an embodiment of the subject invention device.

The ability of the subject meniscal devices to translate yet be self-centering is created by the geometry of the devices in conjunction with the geometries of the femoral condyles and tibial plateaus. The bearing surface geometries of the tibial plateaus and the femoral condyles define the axis of joint rotation of the knee. FIG. 2 shows the shape of the femoral condyle in cross section. FIG. 3 shows the angle (8) of the contour of the femoral condyle relative to the tibial plateau (5) to be such that the planes of symmetry of the respective condyles are not orthogonal to the axis of rotation of the joint, but instead are at angles that converge toward the anterior portion of the particular knee compartment.

The axis of rotation of the tibia on the femur is 90 degrees to the path of the tibial plateau against the femoral condyle. The two tibial plateaus (medial and lateral) are not in the same plane with each other but do act in a relatively constant radius to its respective femoral condyle. In other words, although the symmetry of the device's femoral side may be matched with the femoral condyle while the leg is in full extension, the rotation of the tibial plateau against the femoral condyle is along a constant axis of rotation (90 degrees to the axis of rotation), thus the angularity of the axis of symmetry of the femoral condyle relative to the axis of symmetry of the tibial plateau is not parallel but at some acute angle. Also, the axis of symmetry of the tibial plateau is not parallel to the path of rotation of the tibia relative to the femur but also at some mildly acute angle. Thus, the true orientation of the device, regardless of the relative orientations of symmetry of the tibial side to the femoral side is 90 degrees to the true axis of rotation as described in Hollister et al., "The Axes of Rotation of the Knee", *Clin. Orthopaedics and Rel. Res.*, 290 pp. 259–268, J. B. Lippincott Co., © 1993, herein incorporated by reference. Any localized positions of higher loads are self-limiting due to the ability of the device to translate both rotationally and laterally which mimics the true motion of the natural meniscus as described by Hollister.

The geometry provided by the meniscal device thus mimics the geometry of the tibial plateau with the meniscus intact with respect to the femoral condyle and mimics the geometry of the tibial plateau with the meniscus removed with respect to the tibial plateau, resulting in but little translation relative to the tibia, except for a relatively small rotational and lateral components. With respect to the femoral condyle, however, the device experiences large relative movement, and a rotational component brought about by any difference in the contour angle (22) of the femoral condyle and the concave meniscal device topmost surface (femoral surface). This rotational component further ensures that the device is self-centering, and cannot be "spit" from the joint. In general, the contour angle (22) of the femoral surface of the meniscal device should be within +/-15°, and in general, less than 20°, of the contour angle of the femoral condyle relative to the tibial plateau. Too large an angle will provide too high a centering force, and may accelerate wear of the femoral condyle articular cartilage or the device itself.

In the "rest position," where the knee is in full extension, the outer contours of the meniscal device are designed to substantially mate with the corresponding tibial and femoral surfaces. As the knee is flexed, the mating along the tibial surface is substantially maintained, with only a slight rotation which is resisted due to the fact that the contour angle or orientation of the tibial surface of the meniscal device and the contour angle or orientation of the tibial plateau are the same. However, the contoured mating surfaces of the femoral condyle and femoral meniscal device surfaces can become increasingly dissimilar when the joint articulates, as the contour angles will not necessarily mate correctly throughout the entire articulation cycle. This can cause relative lateral or rotational movement, in the tibial plane, between the femoral condyle and the femoral surface of the meniscal device. The forces generated by the increasingly different geometry creates a rotational moment, in the tibial plane, which is resisted along the mating tibial surfaces but which also results in a restoring force tending to correctly locate the meniscal device along the femoral condyle. Thus, the device is self-centering, in part, as a result of the similar contour angles of the femoral condyle and the femoral surface of the meniscal device.

Generally speaking, each knee presents a different geometry of the respective femoral condyles and tibial plateaus. Even with respect to the right and left knees of a single individual, although bilateral symmetry dictates that the left and right knee components should be mirror images, this is often only an approximation. Thus, the shape of the affected femoral condyle and tibial plateau (while discussed herein in the singular, more than one pair of condyle(s)/plateau(s) may be involved), will have to be ascertained to determine the correct geometry of the meniscal device for a given patient. In some cases, it is desirable to offset the contour angles (from the CSO(30)) of either or both of the meniscal surfaces. This is done to bias the thickness of the meniscal device to the periphery of the device. This would be done, for instance, to accommodate the absence or presence of the meniscus or for some other anatomical reasons.

To implant a meniscal device that possesses the characteristics required by the subject invention, the patient's knee joint may be examined by a non-invasive imaging procedure capable of generating sufficient information such that on appropriately sized and shaped meniscular device may be selected. While a variety of non-invasive imaging devices may be suitable, for example X-ray devices and the like, it is preferable that information as to the size and shape of the meniscal device be provided by magnetic resonance imaging (MRI).

Two methods of non-invasive imaging for selection of a suitable prosthesis are preferred. In the first method, MRI or other non-invasive imaging scans, optionally coupled with exterior measurements of the dimensions of the relevant tibial and femoral portions including the surfaces of the articular cartilage of the tibia and femur, may be used to establish a library of meniscal prostheses whose size and geometry differ according to the age and size of the patient, the patient's genetic make-up, and the like. A limited number of "standard" meniscal device molds are then created, from which corresponding "standard" meniscal devices are produced.

In this first method, a non-invasive imaging scan, such as X-ray or MRI, together with knowledge of the patient's genetic make-up, general body type, extent of the disease, degeneration, or trauma and the like, will enable the surgeon to select a meniscal device of the correct size and shape from the library for the patient. The device is then introduced by arthroscopically assisted implantation, generally limited to extensive clean-up of existing damaged tissue, e.g., torn or particulate natural meniscus damage. It may also be used in conjunction with tibial osteotomy or articular surfacing procedure such as cartilage transplantations or abrasion anthroplasty. Following insertion of the device, X-ray, Fluoroscopy, or MRI may be used to assess the correct positioning of the device both intraoperatively as well as postoperatively. Since the surgical procedures used are not severe, and also not irreversible, an unsuitable device may be readily removed and replaced, either with a different device from a meniscal device library, or by a custom device.

In a second method, each patient receives one or more meniscal devices that are custom tailored for the individual by producing a contour plot of the femoral and tibial mating surfaces and the size of the meniscal cavity. Such a contour plot may be constructed from imaging data, i.e. MRI data, by a suitable computer program. From the contour plot, the correct surface geometry of the meniscal device is determined from the shape of the respective tibial plateau and its contour angle (normally 0 degrees) and offset position, and the shape of the femoral condyle with its contour angle and its offset position. In general, the shapes just mentioned also include the articular cartilage, which, in general, is maintained substantially intact.

The following is an example of the procedure which may be followed to design and construct a meniscal device from MRI data: From MRI image data, the steps described below are preferably taken.

Using MRI data, from an Anterior-Posterior (AP) side view of a medial or lateral compartment of the knee joint, at an angle which positions the view parallel to the AP direction (plane), as shown in FIG. 1, of the femoral condyle when the knee is full extension, the maximum point of contact between the femoral condyle and the tibial plateau is determined by using the particular image section (cut) that represents the maximum femoral extension. The Femoral Cross-section plane (21), FIG. 2, is created normal to this view while the Femoral Sweep plane (8), is in the plane or at an offset angle (22) to the plane of the image (FIG. 1). The intersection of these two planes represents 2 points of the Coordinate System Origin (CSO)(10).

From the Lateral-Medial view (LM), the planar image that represents the maximum femoral extension will also determine the maximum point of contact between the Femoral condyle and the Tibial plateau which represents the $3^{rd}$ point of the CSO (10). The X-axis plane (9) is represented by this (LM) image view and intersects the CSO (10) in the (LM) direction. The Y-axis plane (5) is normal to the X-axis plane (9) and is normal to the (LM) image plane and in the AP plane. The Z-axis plane (12) is normal to the X-axis and is also in the (LM) image plane.

From the (AP) view, with an image that represents the Femoral Sweep plane (8), the radius of curvature of the femoral condyle $R_{FC}$ (2) is determined in the AP view using the following equation: $R_{FC}=(C^2+4H^2)/8H$ where C=the length of a line across the cross-section and H=the height from the midpoint of line C to a point perpendicular on the circumference of the arc which is also the maximum point of contact between the articular surfaces of the respective femoral condyle and the tibial plateau.

Using the same (AP) image, the same procedure is used to determine the radius of curvature of the tibial plateau, $R_{TP}$ (13) in the AP direction (plane). However, this radius must account for the thickness of the meniscus and the meniscal thickness is not included when determining the $R_{TP}$. (13)

From a Lateral-Medial view (LM), a cross-section is viewed of the femoral condyle at the midpoint of the length of the femoral arc (representing the X-axis plane), the same procedure and equation of #1 is used to determine the radius of curvature of the cross sectional radii of both tibial, $R_{TPX}$ (14)(minus the meniscal thickness) and femoral, $R_{FCX}$, surfaces.

Typical values would be $R_{FC}$ (2) from 1.1–2.0 inches, $R_{FCX}$ (3) from 0.5–1.5 inches, $R_{TP}$ (13) from 6–12 inches and $R_{TPX}$ (14) from 1.5–3 inches. In this particular example, the following values were used: $R_{FC}$=1.6 inches, $R_{FCX}$=1.2 inches, $R_{TP}$=10 inches and $R_{TPX}$=2.3 inches From a combination of these same LM and AP views, a determination is made of the current joint spacing and any spacing which would be required to correct any varus or valgus misalignment of the joint. This measurement determines the thickness of the device (17) at the CSO (10) point.

A plane is created in the X-Y plane, which will naturally intersect the CSO, which represents the bottommost surface of the femoral side of the device. This plane is called the Femoral Base Plane (15).

Another plane is created parallel to the Femoral Base Plane, but offset some distance below which corresponds to the desired thickness of the device as determined above. This plane is called the Tibial Base Plane (16). It represents the bottommost surface of the tibial side of the device.

An understanding of the device, and the procedure used to derive its geometry, may be facilitated by the following discussion: Using the following concept: If a ball of radius= 1.0 inches, $R_{FC}$, is placed in a sphere of internal radius=2.0 inches, $R_{TP}$, the area outside the area of immediate contact of the ball on the inner surface of the sphere is represented by a generally circular shape (volume) of constant, wedge shaped cross-section. If a device, representing this circular, wedge shaped volume, were to be placed in the sphere, the ball, when placed into the sphere containing this device, would make intimate contact with both the sphere (at the opening of the device) and the device, thus distributing the load of the ball over a much larger area. Such a device can never escape the sphere without lifting or otherwise dislocating the ball because the ever-increasing thickness of the device (from the wedge shape) will cause increasing levels of interference with the ball as the device is moved in any lateral direction. However, the device may move with the rotation of the ball if the radius of the sphere is close to being concentric with the radius of the ball.

To stop this rotation of the device, one can attach the device (not desired) or (preferred) increase the radius of the sphere (tibial) side up to an approximate order of magnitude larger than the femoral side radius thus inducing a relatively easier motion of the ball on the device versus the device to the sphere or, secondly, use an increasing radius of the sphere side of the device. This has the effect of trying to force a larger radius into a smaller one (which cannot happen). Obviously, this can only be used in one direction, but in the human knee joint, the device will only have a tendency to push from the posterior to the anterior upon knee rotation thus, the radius of curvature on the tibial side of the device, in the Anterior to Posterior direction, is the direction of increasing radii. The amount of increase is small, on the order of 5 to 15% over the length of the device. Either technique or a combination of both can be used to successfully stop the rotation of the device with the femoral condyle ("the ball"). Thus, fixing its position relative to the tibial plateau without attachment.

The concept described in the prior to paragraphs describes the general shape and function of the meniscus found in the normal human knee. Although the meniscus is crescent shaped, the natural anatomy of the knee completes the generally circular shape with the tibial spine, along the central axis of the knee, thus locating the femoral condyle at all times in its range of motion and limiting any potentially harmful positional excursions of the femoral condyle. Since the natural meniscus is attached to the membrane surrounding the knee, it does not need to be attached to the tibial spine to perform this locating function on the femoral condyle. If the shape of the meniscus is damaged or not present then, it cannot perform this locating, load-bearing function. Thus, the loads on the femoral condyle and tibial plateau become more concentrated leading to a gradual, arthritic degeneration of the articular cartilage surface of the femoral condyle. Disease and age can also have this effect.

The purpose of the device is to reduce the concentrated loads on the femoral condyle and its articular cartilage and to maintain proper spatial location of the femoral condyle to the tibial plateau. Since permanent attachment of the device is not desired nor easily accomplished, the circumferential shape of the device is generally kidney shaped to conform to the planar anatomy of the lateral or medial compartments of the knee and due to the differing radii of the femoral and tibial surfaces of the device, the "wedge" shape (FIGS. 5 and 6) required to keep the device centered under the femoral condyle while the condyle moves through its range of motion is naturally present.

Thus, with this understanding of the principal of the device's natural tendency to remain correctly located under the femoral condyle, the amount of "wedge" is determined by the difference in the radii from one surface of the device to the other surface of the device. Further, since the natural meniscus is predisposed to a greater "wedge" on the posterior (11 of FIG. 5) and medial (4 of FIG. 6)(of a medial device, lateral on a lateral device) sides of the femoral condyle, the device can replicate this biased wedge by locating the center of the tibial radii posterior and medial to the CSO (10) of the device. This is accomplished by offsetting the Femoral Sweep Plane (8) and the Tibial Sweep Plane (5) some distance from the CSO (30) as referenced by the Femoral Offset Sweep Plane (20) and the Tibial Offset Sweep Plane (18). The amount of this bias would be determined by the amount of natural meniscus remaining in the knee compartment.

Figures 10, 11:
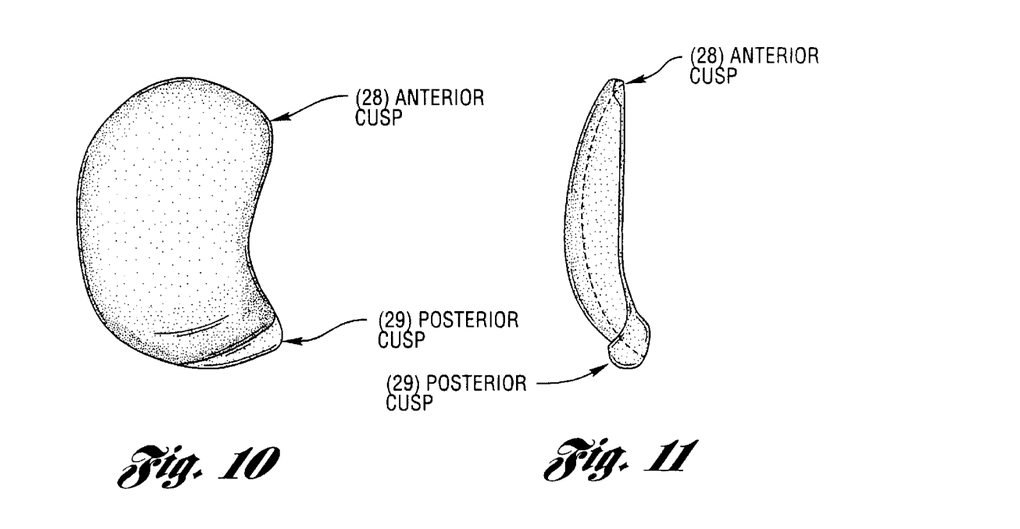
FIG. 10 illustrates one embodiment of a device viewed in plan.
FIG. 11 illustrates the device of FIG. 10 viewed from the side.

In some cases is may be necessary to add "reverse (downward)" curves, or cusps, to the device along two additional planes of revolution, termed the Anterior Cusp Sweep Plane (23) and the Posterior Cusp Sweep Plane (25), generally, as shown in FIGS. 10 and 11, and located along the lateral aspect (of a medial device) of the device at the extreme anterior/lateral (28) and posterior/lateral protrusions (29). Their cross-section shapes are described by the radius of curvature in the respective Anterior Cusp cross-section Plane (24) and Posterior Cusp cross-section Plane (26). The radii of such cusps being on the order of $\frac{1}{10}$ths of inches (several millimeters). Such circumstances would be when there is deformed anatomy or additional stabilization is required of the device.

With the above information, using a parametric design program such as Pro Engineer from Parametric Technology Corporation, a solid block of generally the correct circumferential shape is referenced with a CSO (10) (X,Y,Z origin point)in the middle of the block. From that reference point, Femoral (15) and Tibial (16) Base Planes are established along with the offset (20) and angle (22) of the Femoral Offset Sweep Plane (8) and the offset (18) and angle (0°) of the Tibial Sweep Plane (8). This information, along with the calculated femoral (2,3) and tibial (13,14) radii) is required for proper sizing of the device.

The steps given above may be modified as necessary, and may be combined or accomplished in other than the order given. This process is exemplary only, and not limiting. An example of a particular meniscal device design is as follows:

A femoral offset contour angle (22) of from about 0° to about 45° is suitable, with 5° to about 35° preferable, and an angle in the range of 10°–20° most preferred, in this particular case, 15° (relative to the y axis) was chosen as the femoral offset contour angle. The femoral offset amount (20) was 0.10 inches toward the medial aspect (6), away from the CSO (10) and the y-axis (5). (The femoral offset amount (20) from the CSO on the y-axis has a preferred range of +/−0.20 inches, with +/−0.10 inches being most preferred). The tibial contour angle was 0° (parallel to the y-axis (5)) with a tibial offset amount (18) of 0.20 inches towards the medial aspect. The tibial offset amount (18) from the CSO on the y-axis has a preferred range between −0.20 inches to 0.40 inches with 0.0 inches to 0.20 inches being most preferred. This effectively presents a relative angle of the femoral sweep plane and tibial sweep plane as 15° but with an intersection point (19) that is posterior and medial of the CSO (10), thus creating a wedge shape that is biased to the medial and posterior sides of the device. The offset and angular locations of the Anterior and Posterior Cusp Sweep Planes (23,24,25,26) (if needed), generate the remaining reference planes and cuts in the solid which, after computer processing, will yield the shape of the appropriate device for a particular knee compartment.

It should be noted that prints or photographs of MRI or other non-invasive scans might also be examined and measured manually to produce the needed contour plots. In either case, a SLA model or other rapid prototype model is manufactured to produce a full size prototype which after proof check, is then employed to create a mold suitable for the molding of a custom meniscal device. For example, the CAD/CAM output may be input to a standard stereolithography or other rapid prototyping method device, for example one employing a computer-guided laser beam to cure successively laid down thickness' of photocuring resin as described in U.S. Pat. Nos. 5,109,589; 5,145,908; and 5,496,682, herein incorporated by reference. The result of the stereolithography process is a pattern, generally of an acrylate-type thermoplastic, which may be used in an investment casting operation.

For example, a meniscal device pattern may be imbedded in a sand-type or plaster mold and fired to cause the acrylate polymer to melt and/or decompose, producing a cavity in the mold which is identical in size and shape to the pattern. Alternatively, a stereolithography process employing photocurable ceramic particle dispersion may be used to create the mold itself. Molten metal, fiberre-inforced thermoplastic or thermosetting plastic or the like may then be introduced into the cavity, forming the meniscal device. Gates and flash are cut or machined away, and the meniscal device surfaces smoothed and polished. The finished device is inserted by arthroscopically assisted implantation as previously indicated.

The benefits of the custom meniscal device method as opposed to the library method is that the custom device produced will have a geometry uniquely tailored to the patient's anatomy, and thus more likely to be of correct size and shape. A further advantage is that the custom method is applicable to individuals who, though possibly falling within a group easily identified as requiring a "standard" prosthesis, nevertheless has advanced degeneration or unique trauma which would mitigate against use of a standard device.

Having generally described this invention, a further understanding can be obtained by reference to certain specific examples that are provided herein for purposes of illustration only and are not intended to be limiting unless otherwise specified.

EXAMPLE 1

A 46-year-old male cadaver, with Grade 2 chondromalacia of the tibial plateau of his left medial compartment is subjected to non-invasive MRI imaging of the damaged knee. From the MRI images obtained, contour radii plots and surface descriptions of the femoral condyle and tibial plateau of the affected area, complete with articular cartilage, are generated and analyzed as in the foregoing description. The aforementioned CAD/CAM techniques are used to generate a meniscal device with a femoral AP radius of 1.6 inches, femoral ML radius of 1.2 inches, tibial AP radius of 10 inches, and tibial ML radius of 2.5 inches in accordance with the foregoing description. The difference between the tibial offset angle and the tibial meniscal surface offset angle is selected as 0° with an offset of 0.20 inches towards the medial side from the y-axis. The difference between the femoral condyle contour angle and the tibial meniscal surface contour angle is selected to be 15° with a femoral contour angle offset of 0.15 inches and a tibial contour angle offset of 0.10 inches. From the assembled CAD/CAM data, a stereolithographic pattern is created from which a polished investment cast chrome steel meniscal device is produced.

The cadaver's lower extremity is prepped and draped in a standard fashion. The knee is assessed for the appropriateness of the indications for implantation of the meniscal device (Hallock/Fell Knee). If the indications are met, then a longitudinal incision, approximately 1–3 inches long, is made adjacent to the patellar ligament. The subcutaneous tissue is opened down to the joint capsule that is also opened. The medial compartment of the knee is exposed. Trial sizing of the implant can be performed if necessary. After appropriate size is determined, the implant is introduced into the knee compartment. Applying a varus or valgus stress can facilitate this portion of the procedure. After the implant is in place, the knee is placed through a full range of anatomically correct motion using a modified Instron testing apparatus and stressed to test for any implant displacement. Further checks are performed for stability and fit with X-ray fluoroscopy. Such tests, and in particular the X-ray fluoroscopy, are recorded on videotape and later digitized for further analysis. Only minor translation of the device relative to the tibial plateau was noted and normal translation against the femoral condyle was noted. During the testing and at the end of each test, the device was noted to be in its original position relative to the tibial plateau throughout normal and extra-normal flexing of the knee joint. The tests were repeated with first the anterior cruciate ligament severed, then with the medial collateral ligament severed. In both cases, the meniscal device remained in place without any significant translation relative to the tibial plateau. Further resection of all medial soft tissue, synovium and meniscus was then effected with similar success. Finally the posterior cruciate ligament was severed causing a complete dislocation of the femur from the tibia and at this point the meniscal device was no longer held in place. The use of a non-magnetic meniscal device, such as titanium, also allows for monitoring of the recovery of the damaged articular surface via MRI imaging of the affect joint.

Having now fully described the invention, it will be apparent to one of ordinary skill in the art that many changes and modifications can be made thereto without departing from the spirit or scope of the invention as set forth herein.

What is claimed is:

1. A unicompartmental knee prosthesis suitable for implantation between the femoral condyle and the associated tibial plateau of a knee compartment, comprising a hard body having a substantially elliptical shape in plan, a peripheral portion of said body being of greater thickness than a central portion of said body, said body devoid of physical means of attachment which fix its location in said knee compartment.

2. The prosthesis of claim 1 wherein a cross-section across said device in a plane perpendicular to the plane of said device describes a negative meniscus shape.

3. The prosthesis of claim 1 wherein said body is kidney shaped in plan, a portion of the body indented from an elliptical shape such that the device does not intrude upon the tibial spine of the knee.

4. The prosthesis of claim 1, wherein said body has a portion made of low modulus material.

5. The prosthesis of claim 4, wherein said portion of low modulus material comprises said central portion.

6. The prosthesis of claim 5 wherein said portion of low modulus material is a non-load bearing portion.

7. The prosthesis of claim 1 wherein a section across said body in an anterior-posterior direction has the shape of a substantially symmetrical negative meniscus.

8. The prosthesis of claim 7 wherein a section across said body in a medial-lateral direction has a thickness at a medial periphery which is substantially larger than a thickness at a lateral periphery.

9. The prosthesis of claim 1 wherein a section across said body in a medial-lateral direction has a thickness at a medial periphery which is substantially larger than a thickness at a lateral periphery.

10. The prosthesis of claim 1, wherein said body has a concave femoral top surface and a convex tibial bottom surface.

11. The prosthesis of claim 10, wherein respective radii of said concave femoral top surface and said convex tibial bottom surface are substantially constant.

12. The prosthesis of claim 1 wherein outside edges along said periphery of said device are rounded over to avoid having a sharply defined edge.

13. The prosthesis of claim 1, wherein load bearing portions of said device are comprised of a high modulus material having a hardness greater than 60 on the Shore D scale.

14. The prosthesis of claim 1, wherein said device is comprised of metal, ceramic, or a fiber reinforced polymer.

15. A method of providing a surgically implantable unicompartmental knee prosthesis to a patient in need thereof, said method comprising:
   a) ascertaining the size and shape of a unicompartmental knee prosthesis by examination of said patient; and
   b) selecting a knee prosthesis of claim 1 from a library of knee prosthesis of standard shapes and sizes.

16. The method of claim 15, wherein said examination includes one or more of x-ray imaging and MRI imaging.

17. A method of surgical knee reconstruction of a patient in need thereof, said method comprising:
   a) determining a proper size and shape of a unicompartmental knee prosthesis of claim 1;
   b) selecting a unicompartmental knee prosthesis of said proper size and shape;
   c) surgically exposing the knee compartment; and
   d) implanting said unicompartmental knee prosthesis into said knee compartment.

18. The method of claim 17, wherein said prosthesis is provided by comprising:
   a) ascertaining the size and shape of a unicompartmental knee prosthesis by examination of said patient; and
   b) selecting a knee prosthesis of claim 1 from a library of knee prosthesis of standard shapes and sizes.

19. The method of claim 17, wherein said prosthesis is a custom prosthesis of claim 1 whose size and shape are determined by measuring the dimensions of said knee compartment and determining a size and shape at least partially as a result of said measuring.

20. The method of claim 19 wherein MRI imaging is employed to generate contours of a prosthesis of claim 1, and a custom prosthesis is prepared from said contours.

* * * * *